United States Patent

Raith et al.

[11] Patent Number: 6,060,583
[45] Date of Patent: May 9, 2000

[54] POLYMERIZABLE PHOSPHAZENE DERIVATIVES: A PROCESS FOR PREPARING THEM AND THEIR USES

[75] Inventors: Thomas Raith, Wernau; Wolfgang Nuding, Ulm, both of Germany

[73] Assignee: DaimlerChrysler A.G., Germany

[21] Appl. No.: 09/257,250

[22] Filed: Feb. 25, 1999

Related U.S. Application Data

[62] Division of application No. 08/840,839, Apr. 17, 1997, Pat. No. 5,912,321.

[30] Foreign Application Priority Data

Apr. 27, 1996 [DE] Germany .......................... 196 16 968

[51] Int. Cl.[7] ....................................................... C08J 3/00
[52] U.S. Cl. .................. 528/488; 528/398; 528/397; 526/262; 526/275; 526/276; 548/956; 558/75
[58] Field of Search ..................................... 528/488, 398, 528/397; 526/262, 275, 276; 548/956; 558/75

[56] References Cited

U.S. PATENT DOCUMENTS

| | | | |
|---|---|---|---|
| 4,775,732 | 10/1988 | Lapin | 528/49 |
| 4,874,828 | 10/1989 | Lukacs, III | 526/262 |
| 5,047,270 | 9/1991 | Mori et al. | 428/35.2 |

FOREIGN PATENT DOCUMENTS

| | | |
|---|---|---|
| 0 307 861 | 3/1989 | European Pat. Off. . |
| 0 313 863 | 5/1989 | European Pat. Off. . |
| 0 368 165 | 5/1990 | European Pat. Off. . |
| 0 557 943 | 9/1993 | European Pat. Off. . |
| 43 25 776 | 2/1995 | Germany . |
| 1-158041 | 6/1989 | Japan . |

OTHER PUBLICATIONS

Horn, Hans–Georg, et al., "Polymere mit Phosphor–Stickstoff–Bindungen, 5$^{a)}$", Makromol. Chem., 183; 1833–1841 (1982).

Horn, Hans–Georg, et al., "Polymere mit Phosphor–Stickstoff–Bindungen, 5$^{a)}$", Makromol. Chem., 183; 1843–1854 (1982).

*Primary Examiner*—Duc Truong
*Attorney, Agent, or Firm*—Evenson, McKeown, Edwards & Lenahan, P.L.L.C.

[57] ABSTRACT

This invention relates to a polymerizable phosphazene derivative with a general structural formula

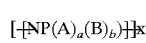

wherein the groups A and B are bonded to phosphorus atoms through —O—, —S—, —NH—, or —NR— (with R=$C_1$–$C_6$ alkyl), and wherein A stands more precisely for a vinyl ether group or a styrene ether group, and B stands more precisely for a hydrocarbon group. The invention also relates to procedures for synthesizing such phosphazene derivatives. The phosphazenes derivatives of the invention can be cured by a process that is initiated cationically, which leads to a large number of advantages. The phosphazene derivatives of the invention can, in particular, be used as curable binders for paints, coatings, fillers, mastics, adhesives, moldings, or films. Paints or coatings comprising the phosphazene derivatives of the invention show especially high mechanical resistance and scratch resistance.

4 Claims, No Drawings

POLYMERIZABLE PHOSPHAZENE DERIVATIVES: A PROCESS FOR PREPARING THEM AND THEIR USES

This application is a division of application Ser. No. 08/840,839, filed Apr. 17, 1997, now U.S. Pat. No. 5,912,321.

This application claims the priority of German patent document 196 16 968.2-43, the disclosure of which is expressly incorporated by reference herein.

BACKGROUND AND SUMMARY OF THE INVENTION

Patent document EP-A-0 557 943 describes phosphazene compounds that can be cured by radical polymerization, the polymerization of which is initiated by adding initiators or by electron radiation. Patent document EP-A-0 368 165 describes curable resin compositions that contain a curable phosphazene compound and a pentaerythritol acrylate compound and/or a bis(4-acryloxydialkoxpheyl)alkane compound mixed together. These known phosphazene derivatives have one or more of the following drawbacks. They tend to polymerize prematurely, so that stabilizers have to be added. High storage temperatures have to be avoided, which in turn results in drawbacks for shelf life and choice of conditions for synthesis, yields, and absence of chlorine. Radical polymerization is inhibited by atmospheric oxygen and thermal curing in particular frequently leads to incompletely hardened surfaces. Curing often occurs very slowly and leads to products that discolor with time. During the curing, severe shrinkage frequently occurs that leads to deterioration of behavior and cracking. So, such phosphazene derivatives, or their mixtures pursuant to the state of the art, cannot be used for many applications, including use as binders for paints and coatings in particular.

The invention makes available new phosphazene derivatives that avoid these drawbacks of the state of the art and provides polymerizable products with improved properties. In particular, it is desirable to avoid a radical mechanism for polymerization of the phosphazene derivatives.

In one aspect, the invention provides polymerizable phosphazene derivatives with the following structural formula

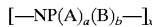

wherein the groups A and B are bonded to phosphorus atoms through —O—, —S—, —NH—, or —NR— (R=$C_1$–$C_6$ alkyl); A contains at least one vinyl ether group of the general formula Q—O—CR'=CHR" and/or styrene ether group of the general formula

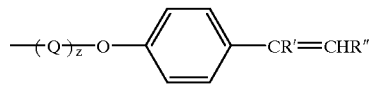

wherein R' and/or R" stands for hydrogen or $C_1$–$C_{10}$ alkyl; B stands for a reactive or nonreactive hydrocarbon group optionally containing O, S, and/or N, and optionally containing at least one reactive group; Q is an aliphatic, cycloaliphatic, aromatic, and/or heterocyclic hydrocarbon group, optionally containing O, S, and/or N; a is a number greater than 0; b is 0 or a number greater than 0 and a +b=2; x stands for a whole number that is at least 2; and z stands for 0 or 1.

The open bonds in the formulae above indicate either joining into a ring with alternating atoms of N and P, or a bonding to groups A or B or the usual catalyst or initiator molecule groups. The later, for example, can be found in Makromol. Chem., 183; 1833–1841 (1982) and Makromol. Chem., 183; 1843–1854 (1982) or can be those of Lewis acids, $SbCl_3$, $AlCl_3$, or sulfur compounds.

The phosphazene derivatives of the invention can contain two or more different vinyl ether groups and/or both vinyl ether groups and styrene ether groups in one molecule. The phosphazene derivatives of the invention, which can be polymerized cationically at least when substituted by vinyl ether groups, and whose polymerization can be initiated by acids, have one or more of the following advantages over known phosphazene derivatives: complete substitution of the phosphazene and thus absence of chlorine can be achieved in high yields; oxygen does not inhibit the curing of the phosphazene derivatives of the invention; even thin coatings are completely cured in the presence of atmospheric oxygen, which makes thermally initiated curing possible in particular; they have no tendency to discolor the polymerized product; they are ordinarily less viscous and therefore more suitable for low-solvent application; and they have less tendency to shrink.

All of these properties make the polymerizable phosphazene derivatives of the invention suitable as curable binders for paints, coatings, fillers, mastics, adhesives, moldings, or films, especially as binders for paints and coatings. For example, they can be used advantageously as binders in transparent coatings for exterior varnishing, or for varnishing interior wood trim in motor vehicles. They can also be used in transparent coatings for polycarbonate headlight diffusion lenses or the like. The usual additive substances such as initiators, pigments, leveling agents, pigments, UV stabilizers, fillers, and the like, can be added to formulations containing the polymerizable phosphazene derivatives of the invention.

The structural formula for the phosphazene derivatives of the invention, shown above, states that they are necessarily at least partially substituted on the phosphorus atoms by groups that contain at least one vinyl ether group and/or styrene ether group, as shown and described. Therefore, the substituent B may be, but does not have to be, present in the phosphazene molecule (i.e., b may be 0).

The phosphazene derivatives of the invention can be cyclic or acyclic compounds, which have a structural skeleton of alternating nitrogen and phosphorus atoms in every case. The cyclic compounds in which x stands for 3 or 4 and which, therefore, consist of 6- or 8-membered rings are preferred. The 6-membered ring, in which x stands for 3, is particularly preferred.

Q is a spacer group that is bonded to a phosphorus atom through an oxygen atom, a sulfur atom, an NH group, or an NR group, and that has at least one vinyl ether group and/or styrene ether group, in which R' and R" have the meanings given above, at its free end and/or as a side group. R' and/or R" in these groups are preferably hydrogen, methyl, or ethyl, and preferably are hydrogen.

Compounds especially preferred according to the invention are those with the general structural formula

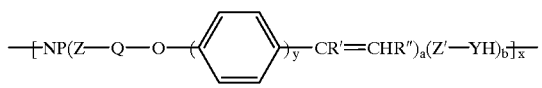

wherein Z and Z' are the same or different and each stands for —O—, —S—, —NH, or —NR— (R=$C_1$–$C_6$ alkyl); Q stands for an aliphatic, cycloaliphatic, aromatic, and/or heterocyclic hydrocarbon group: optionally containing O, S, and/or N; YH stands for an aliphatic, cycloaliphatic, aromatic, and/or heterocyclic hydrocarbon group optionally containing O, S, and/or N and/or optionally containing a reactive group different from a vinyl ether group or a styrene ether group; y is 0 or 1; x stands for a whole number from 2 to 20; and a, b, R', and R" are as defined above.

R in the above formulas is alkyl with 1 to 6 carbon atoms, preferably methyl or ethyl. In the last formula given above, Z and Z' are preferably —O—.

The spacer group Q and the YH group can have such structures that they control the properties of the phosphazene derivative. Thus, the Q and YH groups can have very diverse structures. Examples of such Q and Y groups can be found in German patent document DE-A-4 325 776. They are usually alkaline groups with various chain lengths, straight-chained or branched, preferably with 2 to 20 carbon atoms, and especially with 2 to 6 carbon atoms, biphenylene, phenylene or oxyalkylene groups, or combinations thereof. In the case of oxyalkylene groups, they are preferably oxyalkylene groups with the formula —$(CH_2—CH_2—O)_n$, wherein n is 1 to 20, preferably 1 to 6. The spacer groups Q and Y can optionally contain substituents on this preferred structural formula, or can be interrupted by other groups. Examples of such substituents are ester groups, keto groups, OH groups, or $NH_2$ groups. Examples of groups inserted into the alkaline chain in turn are ester groups, keto groups, urethane groups, or NH groups.

The YH group can be straight-chained or branched, and can consist of a reactive or nonreactive group or can contain a group that differs from the vinyl ether and styrene ether groups of the above formulas. Preferred reactive YH groups are or contain isocyanate groups, carboxyl groups, allyl groups, vinyl acetate groups, N-methylol groups, epoxide groups, glycidyl ether groups, acrylate groups, methacrylate groups, silyl groups (such as $C_1$–$C_6$ alkoxysilyl or aceeoxysilyl groups), OH groups, or $NH_2$ groups. The reactive groups can also be blocked in the usual way. The selection of the YH group, however, is not to be limited to the above enumerated groups.

The preferred phosphazene derivatives of the invention are those in which y is 0 or 1, i.e., those that are vinyl ether derivatives. In any case, they can be cured with cationic initiation using at least one acid. This can be done by direct addition of acid. Instead of this, initiators can be added to the formulation that split off acids when irradiated with UV light or electron beams or when the temperature is raised, which in turn then initiate the polymerization. If the molecule contains other reactive groups in addition to the vinyl ether groups, multicure procedures can be used, for example, combinations of thermal curing, curing by atmospheric humidity or atmospheric oxygen, and UV curing.

The phosphazene derivatives containing styrene ether groups of the invention are ordinarily polymerized in the usual way by a radical mechanism. Thus, optionally, either initiators that split off radicals when irradiated with UV light or in some other way are added, or radicals are generated without addition of initiator by, for example, introducing thermal energy or by, electron irradiation. Anionic or cationic polymerization is also possible in certain cases.

The phosphazene derivatives pursuant to the invention can be prepared by reacting a chlorophosphazene with at least one compound of the general formula MA, alone or in combination with at least one compound of the general formula MB, or successively with MA and MB, in an inert solvent. In these compounds, A and B are as defined above and M stands f or a hydrogen atom, an alkali metal, an alkaline earth metal, or a basic group. The basic group M, for example, can be a pyridyl group or a tertiary amino group such as a triethylamino group, or it can be a 1,8-diazabicyclo[5,4,0]undec-7-ene(1,5-5) group. It is preferred for M to be sodium. The compounds MA and MB can be obtained by reacting the compounds HA and/or HB with sodium hydride, sodium metal, or sodium hydroxide, for example, by the procedure of U.S. Pat. No. 4,775,732 (U.S. Pat. No. 1 4 775 732).

In accordance with the above embodiments, the preferred compounds MA are those with the formula

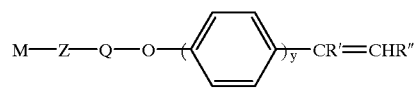

and the compounds MB are those with the general formula M—Z'—YH, wherein M, Z, Z', Q, Y, R', R", and y are as defined above.

The preferred process for preparing the phosphazene derivatives of the invention consists of using compounds MA and MB in which M is bonded to an oxygen atom, and thus Z and Z' stand for —O— in the above preferred formulas for MA and MB. Examples of practical inert solvents in which the reaction is carried out are tetrahydrofuran, toluene, dimethyl sulfoxide, dimethylformamide, chloroform, methylene chloride, and pyridine. Suitable reaction temperatures are between 15 and 110° C., preferably between 18 and 700C, with lower temperatures requiring longer reaction times. Depending on the temperature selected, it is desirable for the reaction times to be between 5 and 60 hours.

DETAILED DESCRIPTION OF THE INVENTION

The invention is described in detail by the following examples.

EXAMPLE 1

The compound 2,2,4,4,6,6-Hexakis(vinyloxyethylenoxy)-2,2,4,4,6,6-hexahydro-1,3,5,2,4,6-triazatriphosphorine is prepared by the following reaction.

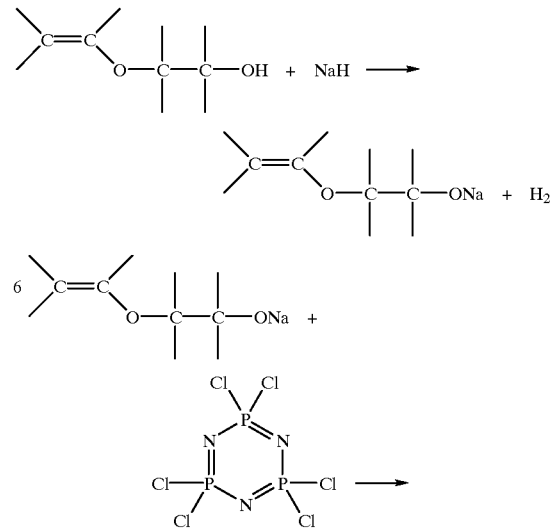

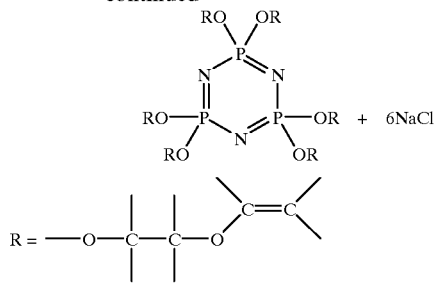

16.80 g (0.10 mole) of sodium hydride (95%) is suspended in 700 ml of anhydrous THF and/or argon in a 2-liter three-necked flask with internal thermometer, dropping funnel, and reflux condenser.

While cooling in an ice bath, 61.67 g (0.70 mole) of ethylene glycol monovinyl ether is then added slowly through a dropping funnel over a period of 90 min. The internal temperature rises slightly, but remains below 20° C. Stirring is then continued at room temperature for a total of 48 h (alternatively 20 h at about 50° C.) The contents of the flask gradually assume a brown color.

A solution of 34.79 g (0.10) mole of phosphonitrile chloride (NPCl$_2$)$_3$ in 200 ml of anhydrous THF is then added slowly (90 min) through a dropping funnel. Water bath cooling is necessary during this addition to keep the temperature below 30° C. Stirring is continued for 1 h longer at room temperature, and the batch is then heated to an internal temperature of 50° C. Stirring is continued overnight (total 24 h) at this temperature.

The mixture is then allowed to cool to room temperature and is filtered by suction. Almost all of the THF is removed from the brown filtrate in a rotary evaporator, 250 ml of diethyl ether and 250 ml of deionized water are added, and the mixture is transferred to a separatory funnel. The ether phase is separated, and the aqueous phase is extracted two more times with 125 ml portions of diethyl ether. The combined ether phases are shaken three times with 50 ml portions of deionized water, which can lighten the mixture considerably. The ether phase is separated and dried over sodium sulfate. After filtering off the drying agent and evaporating the solvent in a rotary evaporator, 62.84 g (0.096 mole, corresponding to 96% of the theoretical amount) of a clear yellow liquid is obtained.

For further purification, the crude product can be stirred with diethyl ether and activated charcoal, filtered through a short silica gel column (Silica Gel 60, mobile phase diethyl ether), and then evaporated. The product is then pure in TLC and HPLC. Yield after purification: 60.23 g (0.092 mole, corresponding to 92% of the theoretical amount). The purified product crystallizes after trituration with a glass rod (crystal nucleation).

The phosphonitrile chloride was recrystallized from n-heptane. The vinyl ether was not further purified. The tetrahydrofuran was stored over Deperox molecular sieve and is anhydrous. The other chemicals are used without additional purification.

Properties of the product:

White, sticky solid; melting point 26–27° C., gradual brown discoloration (without polymerization) above 23° C.; index of refraction (of the noncrystallized liquid) n$_d^{25}$=1.4914.

| Elemental analysis: | | | | | |
|---|---|---|---|---|---|
| | N% | P% | O% | H% | Cl% | O% |
| Calculated: | 6.39 | 14.13 | 43.84 | 6.44 | 0.00 | 29.20 |
| Found: | 6.20 | 14.29 | 44.07 | 6.54 | 0.00 | |

Molecular weight 657.53; readily soluble in chloroform, tetrahydrofuran, diethyl ether, isopropanol, ethyl acetate, toluene, poor solubility in n-heptane, n-pentane; thin layer chromatographic test, developer n-heptane/ethyl acetate 1:1, material silica gel with UV indicator Roth Co., Rf=0.40; detection UV 254 nm; indicator Methyl Red, iodine; Beilstein test for halogens negative.

EXAMPLE 2

2,2,4,4,6,6-Hexakis (vinyloxyhexyloxy)-2,2,4,4,6,6-hexahydro-1,3,5,2,4,6-triazatriphosphorine:

The compound named above is prepared by the process described in Example 1, from 14.42 g (0.10 mole) 1,6-hexanediol divinyl ether, 2.40 g (0.10 mole) sodium hydride, and 4.29 g (0.012 mole) (NPCl$_2$)$_3$.

Properties:

Clear, viscous, slightly yellow-colored liquid; yield 10.64 g (0.011 mole, corresponding to 89% of the theoretical amount); molecular weight 993.57 g/mole; index of refraction n$_d^{25}$=1.4804; Beilstein test for halogens negative; thin layer chromatographic test: mobile phase ethyl acetate, material silica gel with UV indicator Roth Co., Rf=0.27; detection UV 254 nm, indicator Methyl Red, iodine.

EXAMPLE 3

2,2,4,4,6,6-Hexakis(vinyloxybutyloxy)-2,2,4,4,6,6-hecxahydro-1,3,5,2,4,6-triazatripnosphorine:

This compound is prepared by the method described in Example 1 from 11.62 g (0.10 mole) 1,4-butanediol divinyl ether, 2.40 g (0.10 mole) sodium hydride, and 4.97 g (0.014 mole) (NPCl$_2$)$_3$.

Properties:

Clear, viscous, pale yellow-colored liquid; yield 7.60 g (0.009 mole corresponding to 67% of the theoretical amount), molecular weight 825.39 g/mole; index of refraction n$_d^{25}$=1.4814; Beilstein test for halogens negative; thin layer chromatographic test: mobile phase n-haptene/ethyl acetate 1:1; material silica gel with UV indicator Roth Co., Rf=0.55, detector UV 254 nm, indicator Methyl Red, iodine.

EXAMPLE 4

2,2,4,4,6,6-Hexakis[vinyloxydl(ethylenoxy)]-2,2,4,4,6,6-hexahydro-1,3,5,2,4,6-triaztriphosphorine:

This compound is prepared by the method described in Example 1, with a somewhat longer reaction time, from 13.27 g (0.10 mole) diethylene glycol; monovinyl ether, 2.40 g (0.10 mole) sodium hydride, and 4.97 g (0.014 mole) (NPCl$_2$)$_3$ Properties:

Clear, viscous, slightly yellow-colored liquid; yield 9.68 g (0.011 mole, corresponding to 75% of the theoretical amount), molecular weight 921.36 g/mole; Beilstein test for halogens negative; thin layer chromatographic test: mobile phase ethyl acetate; material silica gel with UV indicator Roth Co., Rf=0.70, detector UV 254 nm, indicator Methyl Red, iodine; readily soluble in dichloromethane, chloroform, tetrahydrofuran; poor solubility in water, n-haptene.

EXAMPLE 5

The compound 2,2,4,4,6,6-Hexakis(3'-vinyloxypropylamino)-2,2,4,4,6,6-hexahydro-1,3,5,2,4,6-triazatriphosphorine is prepared by the following reaction:

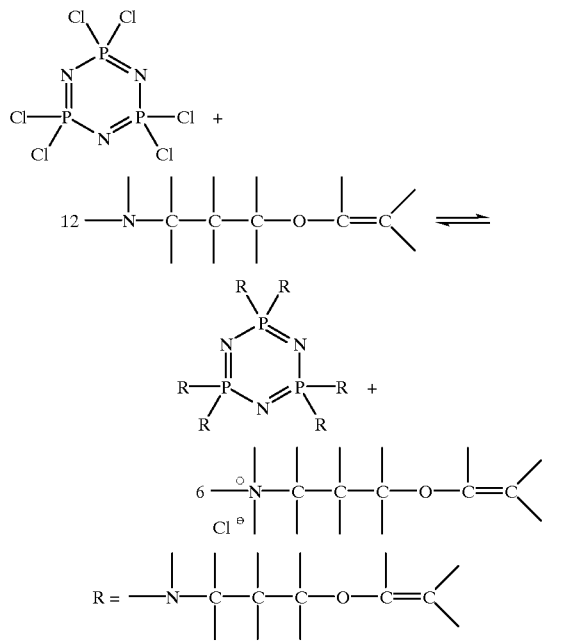

20.23 g (0.20 mole) of 3-amino-1-propanol vinyl ether is placed in a 259-ml three-necked flask with dropping funnel, reflux condenser, and internal thermometer, and 50 ml of anhydrous toluene is added. A solution of 4.97 g (0.014 mole) of $(NPCl_2)_3$ in 50 ml of toluene is-then added over a period of 20 min while cooling with a water bath. The internal temperature rises slightly. After the addition is about half complete, a white precipitate of hydrochloride is formed. Stirring is continued for 150 min at room temperature, and the mixture is then heated to an internal temperature of 50° C. The mixture is stirred at this temperature for 18 h, and is then allowed to cool to room temperature. The mixture is filtered by suction, and the filtrate is shaken with 15 ml of deionized water, dried over anhydrous sodium sulfate, and filtered. The solvent is then drawn off from the organic phase obtained in a rotary evaporator. After brief drying under high vacuum, 12.21 g of an orange, highly viscous, clear liquid is obtained.

The product is taken up in toluene and filtered through a short: silica gel column (Silica Gel 60); yield after removal of solvent and drying under high vacuum 9.70 g (0.013 mole, corresponding to 94% of the theoretical amount) of clear, yellow, highly viscous liquid.

Properties:

Molecular weight 735.78 g/mole; thin layer chromatographic test: mobile phase ethyl acetate, material silica gel, with UV indicator Roth Co., Rf=0.80; detection: indicator MethYl Red, iodine.

EXAMPLE 6

Vinyl ether phosphazene derivative with mixed substitution are prepared according to the following reaction:

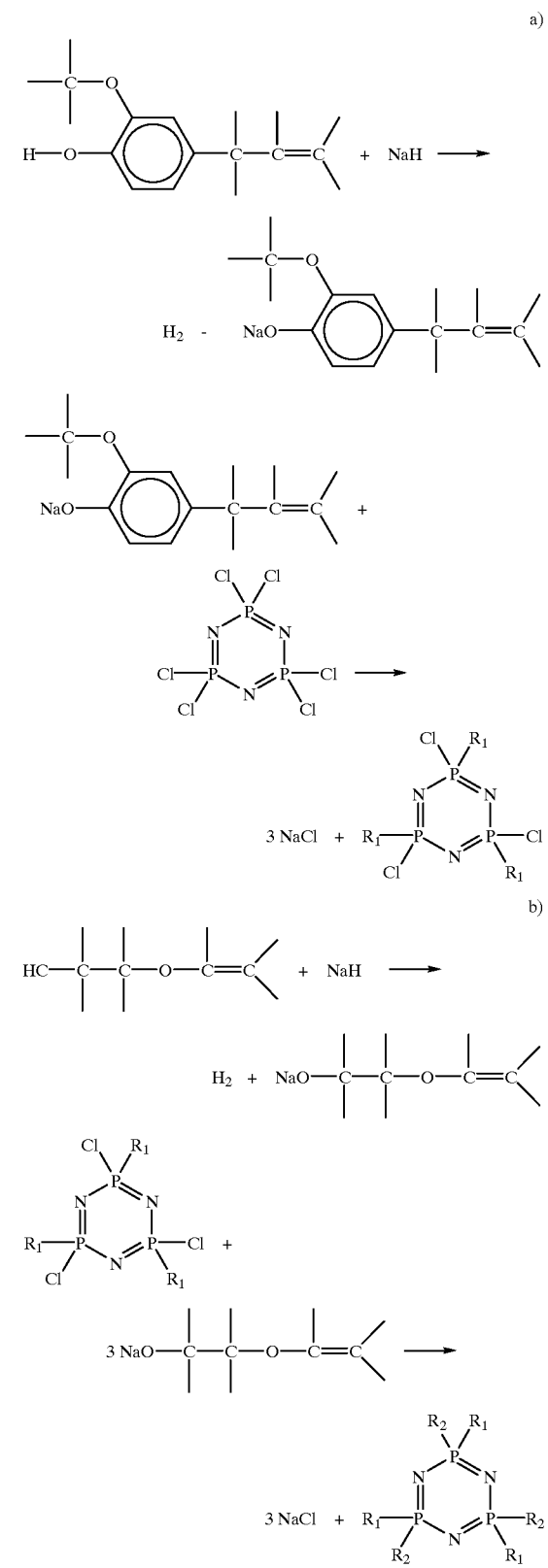

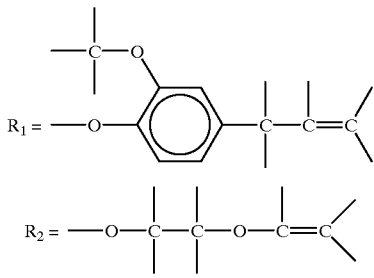

a) 9.60 g (0.40 mole) of sodium hydride is placed in a 1000-ml three-necked flask with KPG stirrer, dropping funnel, and internal thermometer, and is slurred with 100 ml of anhydrous tetrahydrofuran. While cooling with ice/salt, a solution of 65.68 g (0.40 mole) of eugenol in 50 ml of anhydrous tetrahydrofuran is then added dropwise (gas evolution, addition time 45 min).

Stirring is continued for 1 h at room temperature, and then a solution of 46.36 g (0.133 mole) of $(NPCl_2)_3$ in 150 ml of anhydrous tetrahydrofuran is added, likewise while cooling with ice/salt (addition time 15 min, gelatinous precipitation of NaCl, flask contents gray-green).

The mixture is stirred for 60 h at room temperature, transferred to a single-necked flask, and the solvent is evaporated by rotation. The product is taken up in 150 ml of diethyl ether and 150 ml of deionized water, and the phases are separated in a separatory funnel. The aqueous phase is washed twice with 10 ml portions of deionized water. The combined orange-colored ether phases are dried over anhydrous sodium sulfate. The drying agent is filtered off and the clear filtrate is stirred for 30 min at room temperature with activated charcoal. After repeated filtration and solvent removal by rotary evaporation, 94.94 g (0.130 mole, corresponding to 98% of the theoretical amount) of a viscous, clear, brown-colored liquid is obtained.

For purification, the product is filtered through a short silica gel column (Silica Gel 60) mobile phase n-heptane/ethyl acetate 1.1). The solvent is removed by rotary evaporation and the product is dried on an oil pump. Yield 87.62 g (0.120 mole, corresponding to 90% of the theoretical amount) of highly viscous, light yellow clear liquid.

Properties of the intermediate:

Molecular weight 730.89 g/mole; Beilstein test for halogen positive; index of refraction $n_d^{20}$–1.5723; readily soluble in toluene, chloroform, ethyl acetate, diethyl ether, tetrahydrofuran, acetone; poor solubility in water, n-heptane; the product consists of isomeric compounds.

| | Elemental analysis: | | | | | |
|---|---|---|---|---|---|---|
| | C% | H% | N% | O% | Cl% | P% |
| Calculated: | 49.38 | 4.56 | 5.76 | 13.10 | 13.39 | 12.76 |
| Found: | 49.63 | 4.66 | 5.61 | | 14.61 | 12.81 |

Thin layer chromatographic test: developer ethyl acetate; material silica gel with UV indicator Roth Co., Rf=0.71; detection UV 254 nm, indicator Methyl Red, iodine.

b) 4.46 g (0.144 mole) of sodium hydride is placed in a 250-ml three-necked flask with dropping funnel, reflux condenser, and internal thermometer, and is slurried with 100 ml of anhydrous tetralydrofuran. The mixture is stirred for 5 min, and a solution of 12.69 g (0.144 mole) of ethylene glycol monovinyl ether in 20 ml of anhydrous tetrahydrofuran is then added over a period of 30 min while cooling with a water bath. The mixture is then heated to an internal temperature of 50° C. and stirred for 40 hours. The flask contents are then cooled down to room temperature.

While cooling with a water bath, a solution of 30.00 g (0.041 mole) of $(NP[O\text{—}C_6H_3\{OCH_3\}C_3H_5]Cl)_3$ in ~70 ml of anhydrous tetrahydrofuran is then added dropwise over a period of 1 hour. The mixture is stirred for 3 h at room temperature and is then heated to an internal temperature of 50° C. After stirring for 40 h at the temperature the brown contents of the flask are allowed to cool to room temperature, transferred to a single-necked flask, and the solvent is evaporated by rotation. The product is taken up in 130 ml deionized water and 130 ml of chloroform, and the phases are separated in a separatory funnel. The aqueous phase is again shaken with 50 ml of chloroform. The combined organic phases in turn are washed twice with 50 ml portions of 5% sodium chloride solution, and then dried over anhydrous sodium sulfate. After filtering off the drying agent, removing the solvent by rotary drying, and drying under high vacuum, 35.83 g (0.040 mole, corresponding to 99% of the theoretical amount) of a pasty, caramel-colored compound is obtained.

For purification, the product is stirred with activated charcoal and filtered through a short silica gel column (Silica Gel 60). After drawing the solvent off from the filtrate and drying the product under high vacuum, 28.37 g (0.032 mole, corresponding to 78% of the theoretical amount) of pale-colored pasty product is obtained.

Properties of the end product:

Molecular weight 885.2 g/mole; Beilstein test for halogen negative; thin layer chromatographic test: mobile phase n-heptane/ethyl acetate 1:1; material silica gel with UV indicator Roth Co., Rf=0.47; detection UV 254 nm, indicator Methyl Red, iodine.

| | Elemental analysis: | | | | | |
|---|---|---|---|---|---|---|
| | C% | H% | N% | O% | Cl% | P% |
| Calculated: | 56.95 | 6.14 | 4.74 | 21.67 | 0.00 | 10.19 |
| Found: | 57.41 | 6.33 | 4.68 | | 0.00 | 11.00 |

EXAMPLE 7

The compound 2,2,4,4,6,6-Hexakis(styrenoxy)-2,2,4,4,6,6,-hexahydro-1,3,5,2,4,6-triazatriphosphorine is prepared according to the following reaction:

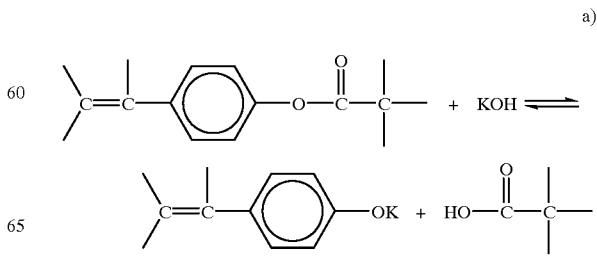

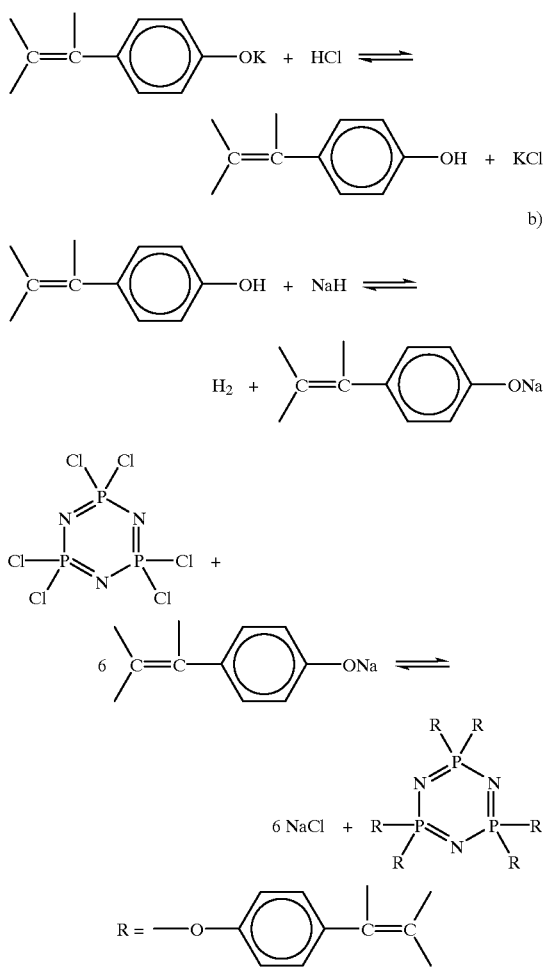

a) 38.88 g (0.24 mole) of p-acetoxystyrene is placed in a 500-ml three-necked flask with internal thermometer, and 400 ml of a 10% potassium hydroxide solution is added over a period of 2 min while stirring and cooling in a water bath. The flask contents turn yellow, two phases form, and the internal temperature rises slightly. The mixture is first stirred for 2 h longer while cooling in a water bath, and is then stirred overnight at room temperature (about 15 h).

On the next day, the contents of the flask are orange-colored and consist of one phase only. It is neutralized with about 175 ml of 3 N hydrochloric acid (pH control). The voluminous product precipitates out. It is filtered off by suction and washed with some n-heptane. The crude product is dried under oil pump vacuum to determine the crude yield.

Crude yield 24.84 g (0.207 mole, corresponding to 86% of the theoretical amount) of light pink powder. It is dissolved in 200 ml of chloroform and shaken twice with 50 ml portions of deionized water. The organic phase is dried over anhydrous sodium sulfate and, after filtering off the drying agent, it is stirred for 10 min with activated charcoal. It is filtered repeatedly and the solvent is drawn off in a rotary evaporator.

Crude yield was 18.11 g (0.151 mole, corresponding to 63% of the theoretical amount) of white powder. For further purification, it is recrystallized from a mixture of 100 ml of chloroform and 50 ml of n-heptane (white crystals form quickly on standing in a refrigerator). Yield after suction filtration and drying was 12 84 g (0.107 mole, corresponding to 54% of the theoretical amount) of white powder. The prepared p-hydroxystyrene should be used immediately since it can become discolored on lengthy storage.

Properties of p-hydroxystyrene:

White solid; melting point 68 to 70° C.; molecular weight 120.15 g/mole, readily soluble in acetone, tetrahydrofuran, ethanol, diethyl ether, poorly soluble in n-heptane, water; thin layer chromatographic test: developer n-heptane/ethyl acetate 1:1; material silica gel with UV indicator Roth Co., Rf=0.50; detection UV 254 nm, indicator Methyl Red, iodine.

| | Elemental analysis: | | |
|---|---|---|---|
| | C% | H% | O% |
| Calculated: | 79.97 | 6.71 | 13.32 |
| Found: | 79.73 | 6.66 | | b) 2.08 g (0.087 mole) of NaH is suspended in 130 ml of anhydrous tetrahydrofuran in a 500 ml three-necked flask and the mixture is stirred for 5 min at room temperature. A solution of 12.84 g of p-hydroxystyrene and 0.01 g of sulfur (inhibitor) in 100 ml of anhydrous tetrahydrofuran is then added dropwise over a period of 30 min (gas evolution, rise of internal temperature to 30° C.; the contents of the flask quickly become brown-colored).

The mixture is stirred for 30 min longer at room temperature, and the alkoxide formation is then complete (no further evolution of gas, clear brown solution). A solution of 3.77 g (0.011 mole) of $(NPCl_2)_3$ (recrystallized from n-heptane) in 40 ml of anhydrous tetrehydrofuran is then added dropwise over a period of 15 min (slight internal temperature rise). After the addition is complete, stirring is continued for 1 h longer at room temperature, and the mixture is then heated to an internal temperature of 60° C. (immediate precipitation of NaCl). Stirring is continued overnight at this temperature (15 h in all).

The mixture is allowed to cool to room temperature and the contents of the flask are transferred with a little tetrahydrofuran into a 1-liter round-bottomed flask. Most of the solvent is evaporated by rotation, and the crude product is transferred into a separatory funnel by means of 100 ml or diethyl ether and 100 ml of deionized water. The phases are separated, and the brown aqueous phase is extracted twice with 50 ml portions of diethyl ether. The combined ether phases (yellow-orange) are shaken in succession with 30 ml each of 2 N hydrochloric acid, 5% sodium carbonate solution, and 5% sodium chloride solution, and are then dried over anhydrous sodium sulfate. The mixture is filtered, the filtrate is stirred for 10 minutes with activated charcoal, filtered again, and the ether is evaporated by rotary evaporation. Crude yield was 11.90 g (0.014 mole, corresponding to>100% of the theoretical amount) of white powder.

For further purification, the product is recrystallized from So ml of isopropanol. Final yield was 7.90 g (0.009 mole, corresponding to 85% of the theoretical amount) of white powder.

Properties:

White solid; melting point 99 to 100° C.; thermal behavior: gradual polymerization above 120° C.: molecular weight 849.89 g/mole; readily soluble in tetrahydrofuran, dichlcromethane, diethyl ether, toluene, acetone; poorly soluble in water, n-heptane; thin layer chromatographic test: developed system n-heptane/ethyl acetate 1:1; material silica gel with UV indicator Roth Co., Rf=0.03; detection UV 254 nm, indicator Methyl Red, iodine; Beilstein test for halogens negative.

| | Elemental analysis: | | | | | |
|---|---|---|---|---|---|---|
| | C% | H% | N% | O% | Cl% | P% |
| Calculated: | 67.84 | 4.98 | 4.94 | 11.30 | 0.00 | 10.93 |
| Found: | 67.88 | 5.12 | 4.82 | | 0.00 | 10.76 |

What is claimed is:

1. A process for preparing a phosphazene derivative comprising reacting a chlorophosphazene in an inert solvent with at least one compound of the general formula MA, alone or in combination with at least one compound of the general formula MB, or in succession with MA and MB, wherein A contains at least one of a vinyl ether group of the general formula Q—O—CR'=CHR" and a styrene ether group of the general formula

wherein at least one of R' and R" are hydrogen or a $C_1$–$C_{10}$ alkyl group;

B is a reactive or nonreactive hydrocarbon group optionally containing at least one of O, S, and N, and optionally containing at least one reactive group;

Q is one of an aliphatic, cycloaliphatic, aromatic, and heterocyclic hydrocarbon group optionally containing at least one of O, S, and N; and M is selected from the group consisting of hydrogen, an alkali metal, an alkaline earth metal, or a basic group.

2. The process of claim 1, wherein MA is a compound of the general formula

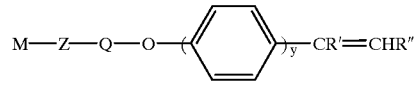

and a MB is a compound of the general formula M—Z'—YH, wherein Z and Z' are the same or different and each stands for —O—, —S—, —NH—, or —NR— wherein R is a $C_1$–$C_6$ alkyl; Q is at least one of an aliphatic, cycloaliphatic, aromatic, and heterocyclic hydrocarbon group optionally containing at least one of O, S, and N; YH stands for at least one of an aliphatic, cycloaliphatic, aromatic, and heterocyclic hydrocarbon group optionally containing at least one of O, S, and N and optionally containing a reactive group different from a vinyl ether group or a styrene ether group;

y is 0 or 1; x is a whole number from 2 to 20; and a, b, R' and R" are defined as in claim 1.

3. The process of claim 1, further comprising obtaining MA and optionally MB by reacting HA and HB with sodium hydride, sodium, or sodium hydroxide, wherein M in MA and optionally MB is sodium.

4. The process of claim 1, wherein M is a pyridyl group or a tertiary amino group.

* * * * *